(12) United States Patent
Couronne et al.

(10) Patent No.: US 9,681,830 B2
(45) Date of Patent: Jun. 20, 2017

(54) DEVICE AND METHOD FOR DETECTING A VITAL PARAMETER

(75) Inventors: Robert Couronne, Erlangen (DE); Fabio Ciancitto, Erlangen (DE); Sergey Ershov, Erlangen (DE); Christian Weigand, Cadolzburg (DE); Hans-Josef Gassmann, Meerbeck (DE); Rainer Haevescher, Stemwede (DE)

(73) Assignees: Fraunhofer-Gesellschaft zur Foerderung der angewandten Forschung e.V., Munich (DE); ZF Friedrichshafen AG, Friedrichshafen (DE)

( * ) Notice: Subject to any disclaimer, the term of this patent is extended or adjusted under 35 U.S.C. 154(b) by 1187 days.

(21) Appl. No.: 13/081,186

(22) Filed: Apr. 6, 2011

(65) Prior Publication Data
US 2011/0237912 A1    Sep. 29, 2011

Related U.S. Application Data

(63) Continuation of application No. PCT/EP2009/006875, filed on Sep. 23, 2009.

(30) Foreign Application Priority Data

Oct. 7, 2008  (DE) .................. 10 2008 050 638
Nov. 6, 2008  (DE) .................. 10 2008 056 251

(51) Int. Cl.
*A61B 5/1455*  (2006.01)
*A61B 5/00*  (2006.01)

(52) U.S. Cl.
CPC ........ *A61B 5/14551* (2013.01); *A61B 5/6893* (2013.01); *A61B 2560/0209* (2013.01)

(58) Field of Classification Search
USPC ................................ 600/310, 322, 323, 324
See application file for complete search history.

(56) References Cited

U.S. PATENT DOCUMENTS

| 3,911,899 A | 10/1975 | Hattes |
| 4,122,427 A | 10/1978 | Karsh |

(Continued)

FOREIGN PATENT DOCUMENTS

| CA | 2517184 | 8/2005 |
| DE | 3723880 | 1/1989 |

(Continued)

OTHER PUBLICATIONS

Int'l Search Report, mailed Feb. 3, 2010, in related PCT application No. PCT/EP2009/006875, 12 pages.

(Continued)

*Primary Examiner* — Eric Winakur
(74) *Attorney, Agent, or Firm* — Perkins Coie LLP; Michael A. Glenn

(57) ABSTRACT

A device for detecting a vital parameter is described, comprising: an optoelectronic sensor arrangement for detecting the vital parameter by means of light remission at a finger, wherein the optoelectronic sensor arrangement has a first light source for generating light in a visible wavelength range, a second light source for generating light in a non-visible wavelength range and a light-sensitive element; and a controller which is implemented to switch on the second light source in temporal intervals, execute an evaluation of the light received from the light-sensitive element in the invisible wavelength range of the second light source with respect to whether a finger is applied to the optoelectronic sensor arrangement and to switch on the first light source as soon as the evaluation indicates that a finger is applied to the optoelectronic sensor arrangement.

7 Claims, 4 Drawing Sheets

(56) References Cited

U.S. PATENT DOCUMENTS

| | | | |
|---|---|---|---|
| 4,773,422 A | | 9/1988 | Isaacson et al. |
| 4,967,751 A | | 11/1990 | Sterzer |
| 5,746,697 A | * | 5/1998 | Swedlow et al. ............ 600/323 |
| 5,792,052 A | | 8/1998 | Isaacson et al. |
| 5,825,293 A | | 10/1998 | Ahmed et al. |
| 6,439,333 B2 | | 8/2002 | Domens et al. |
| 6,513,164 B1 | | 2/2003 | Hearns et al. |
| 6,697,658 B2 | * | 2/2004 | Al-Ali ........................ 600/323 |
| 6,832,987 B2 | | 12/2004 | David et al. |
| 7,499,740 B2 | * | 3/2009 | Nordstrom et al. ......... 600/323 |
| 7,673,354 B2 | | 3/2010 | Fader |
| 2003/0036685 A1 | | 2/2003 | Goodman |
| 2003/0208109 A1 | | 11/2003 | David et al. |
| 2004/0077937 A1 | | 4/2004 | Yarden |
| 2004/0133082 A1 | | 7/2004 | Abraham-Fuchs et al. |
| 2004/0245344 A1 | | 12/2004 | Fischer et al. |
| 2005/0084075 A1 | | 4/2005 | Kotzin |
| 2005/0239075 A1 | | 10/2005 | Yanagidaira et al. |
| 2006/0009685 A1 | | 1/2006 | Finarov |
| 2006/0058595 A1 | | 3/2006 | Herrmann |
| 2006/0250275 A1 | | 11/2006 | Rodemer et al. |
| 2008/0103702 A1 | | 5/2008 | Ando et al. |
| 2008/0243018 A1 | | 10/2008 | Zuhars et al. |
| 2009/0082989 A1 | | 3/2009 | Zuhars et al. |
| 2010/0240972 A1 | * | 9/2010 | Neal ........................... 600/324 |
| 2011/0218409 A1 | | 9/2011 | Kugler et al. |

FOREIGN PATENT DOCUMENTS

| | | |
|---|---|---|
| DE | 29901849 U1 | 5/1999 |
| DE | 10249415 B3 | 3/2004 |
| DE | 10 2004 007253 B3 | 6/2005 |
| DE | 102004010554 | 9/2005 |
| DE | 102005059687 | 6/2007 |
| DE | 102006005664 | 8/2007 |
| DE | 202006012071 | 10/2007 |
| DE | 102008016286 | 10/2008 |
| EP | 1632371 | 3/2006 |
| EP | 1661511 | 5/2006 |
| GB | 2390460 | 1/2004 |
| JP | 2001-260698 | 9/2001 |
| JP | 2001245871 | 9/2001 |
| WO | WO-9613208 | 5/1996 |
| WO | 9835118 | 8/1998 |
| WO | WO-2005/009237 | 2/2005 |

OTHER PUBLICATIONS

Hug, Rene; "Le pouls au volat . . . "; Apr. 14, 2005; 2 pages (including translation).

Mead, et al., "Pulmonary Ventilation Measured from Body Surface Movements", Science, vol. 156, 1967, pp. 1383-1384.

Jeong, in Cheol et al., "Development of Bio Signal Measurement System for Vehicles", 2007 International Conference on Convergence Information Technology, IEEE, Piscataway, NJ, USA, Nov. 21, 2007 (Nov. 21, 2007), p. 1091-1096.

* cited by examiner

DEVICE AND METHOD FOR DETECTING A VITAL PARAMETER

CROSS-REFERENCE TO RELATED APPLICATIONS

This application is a continuation of copending International Application No. PCT/EP2009/006875, filed Sep. 23, 2009, which is incorporated herein by reference in its entirety, and additionally claims priority from German Applications Nos. DE 102008050638.9, filed Oct. 7, 2008 and DE 102008056251.3, filed Nov. 6, 2008, which are all incorporated herein by reference in their entirety.

BACKGROUND OF THE INVENTION

The present invention relates to devices and methods for detecting a vital parameter and, for example, to the control of optoelectronic sensor arrangements used for this purpose.

The methods of optical plethysmography and pulse oxymetry are methods for a none invasive determination of vital parameters of a living being, e.g., of the pulse rate, the pulse rate variability and the arterial oxygen saturation, by measuring a light absorption or a light remission in the tissue of the living being.

Typically, the oxygen saturation values or $SpO_2$ values are tapped via an optical sensor at the finger, toe or earlobe, wherein measuring is executed by means of a clip sensor or an adhesive sensor.

The application of optical plethysmography and pulse oxymetry for detecting such vital parameters may, however, also be executed under automobile conditions, i.e., in a automobile or a vehicle, for example by integrating the optical sensors into operating elements of the vehicle. This enables a detection of the vital parameters with little adverse effects on the driver. One possible implementation is the integration of the optical sensor into a gear level knob of the vehicle.

The sensors typically consist of two light sources, e.g., a red diode and an infrared diode and a photo sensor or photodiode. As soon as the optical sensor is switched on, the two diodes light up. The infrared diode radiates in the non visible range of the electromagnetic spectrum, in contrast to that the red diode radiates in the visible range of the electromagnetic spectrum. On the one hand this may distract the driver and on the other hand it may negatively affect the light design of the interior of the vehicle, e.g., when the predominant color is green or blue.

SUMMARY

According to an embodiment, a device for detecting a vital parameter may have an optoelectronic sensor arrangement for detecting the vital parameter by means of light remission, wherein the optoelectronic sensor arrangement comprises a first light source for generating light in a visible wavelength range, a second light source for generating light in a non-visible wavelength range and a light sensitive element; and a control means which is implemented to switch on the second light source in temporal intervals, execute an evaluation of the light received from the light-sensitive element in the invisible wavelength range of the second light source with respect to whether a finger is applied to the optoelectronic sensor arrangement and to switch on the first light source as soon as the evaluation indicates that a finger is applied to the optoelectronic sensor arrangement.

According to another embodiment, a method may have the step of detecting a vital parameter by means of an optoelectronic sensor arrangement for detecting the vital parameter by means of light remission, wherein the optoelectronic sensor arrangement comprises a first light source for generating light in the visible wavelength range, a second light source for generating light in a non-visible wavelength range and a light-sensitive element, and wherein the method may further have the steps of switching on the second light source in temporal intervals; evaluating the light received from the light-sensitive element in the invisible wavelength range of the second light source with respect to whether a finger is applied to the optoelectronic sensor arrangement; and switching on the first light source as soon as the evaluation indicates that a finger is applied to the optoelectronic sensor arrangement.

According to another embodiment, a device for detecting a vital parameter may have an optoelectronic sensor arrangement for detecting the vital parameter by means of light remission at a finger, wherein the optoelectronic sensor arrangement comprises a first light source for generating light in a visible wavelength range, a second light source for generating light in a non-visible wavelength range and a light sensitive element; and a controller which is implemented to switch on the second light source in temporal intervals, execute an evaluation of the light received from the light-sensitive element in the invisible wavelength range of the second light source with respect to whether a finger is applied to the optoelectronic sensor arrangement and to switch on a first light source as soon as the evaluation indicates that a finger is applied to the optoelectronic sensor arrangement, wherein the controller is implemented to execute an evaluation over a temporal course of the light received from the light sensitive element in the invisible wavelength range of the second light source to detect a pulse parameter when a finger is applied to the optoelectronic sensor arrangement and to switch on the first light source when a pulse wave is detected.

Further embodiments of the present invention provide a method for controlling the switch-on arrangement of the optical sensor for the detection of pulse waves, pulse rate, pulse rate variability and oxygen saturation of the blood of the driver of the vehicle. Here, the operation of the sensor is made optically invisible for the user.

As explained above, the continuous operation of the active sensor module which includes two light emitting diodes, when the finger is not applied, may lead to the impairment of the driver on the one hand and, on the other hand, of the light design in the vehicle interior. These effects are in particular disturbing in the hours of evening and night. Embodiments of the present invention cause the switch-off of the diode emitting the visible light at times at which no finger is applied to the optoelectronic sensor arrangement or to the active sensor module. This way the disturbing impairment of driver and light design may effectively be prevented.

Further, by switching off the diode emitting the visible light, the overall energy consumption of the transmitter is reduced.

In the present application, for the term "optoelectronic sensor arrangement" generally also the terms sensor or sensor module are used. Further, a red diode forms an embodiment for the first light source which is implemented to generate light in the visible wavelength range or in the visible electromagnetic spectrum, an infrared diode forms an embodiment for the second light source which is implemented to generate light in the non-visible wave length range or in the non-visible electromagnetic spectrum, and a photosensor or a photodiode forms an embodiment for a light-sensitive element. Further, the term "vital parameter" is a generic term for medical parameters such as e.g., for blood oxygen saturation, the pulse, the electrocardiogram (ECG), the temperature, muscle tension, blood sugar content or blood pressure. Here, with respect to the "pulse", a difference may be made between the pulse parameters or pulse information of pulse wave, pulse frequency, pulse amplitude, shape of the pulse wave and/or the speed of propagation of the pulse wave.

Embodiments of the invention, thus, also relate to a technical solution for controlling the switch-on arrangement of an optical sensor for the detection of a pulse wave, pulse rate, a pulse rate variability and an oxygen saturation of the blood of a driver of a vehicle.

Fields of application of the embodiments are, for example, in the field of preventive, monitoring and attending medicine for the use in a vehicle, e.g., as a driver assistance system.

BRIEF DESCRIPTION OF THE DRAWINGS

In the following, embodiments of the present invention are explained in more detail with reference to the accompanying drawings.

In the description, for objects and functional units comprising the same or similar functional characteristics, the same reference numerals are used, wherein a repeated description of these objects and functional units is omitted.

DETAILED DESCRIPTION OF THE INVENTION

As mentioned above, a continuous activation of the first light source generating light in the visible wave length range would disturb the driver, in particular in the hours of evening and night and/or disturb the light design of the vehicle interior.

For a better understanding of the present invention, first of all as an example, a sensor for detecting a vital parameter is described which comprises a red and an infrared diode as light sources, and a photosensor or a photodiode as a light-sensitive element. The light sources and the photosensor are, for example, arranged in the same plane and are arranged close to each other. The light sources radiate their light into the tissue of the finger and the photosensor measures the reflected, remitted portions of the light field. The tissue is continuously supplied with blood, wherein circulation is not constant but varies with time in the form of the pulse waves. The blood has the characteristic to absorb the light differently in different wavelengths. The degree of absorption of the light field or the reflected portion of the light field in the temporal course provides information on the pulse waves in the tissue. Here, for detecting characteristics of the pulse wave (e.g., the shape, the speed of propagation, the pulse rate) the determination of the absorption degree of only one light wavelength is sufficient, i.e., in the visible or non-visible wavelength range. For calculating the oxygen saturation of the blood, however, two light wavelengths or the determination of the absorption degree for two light wavelengths are needed.

Figure 1:
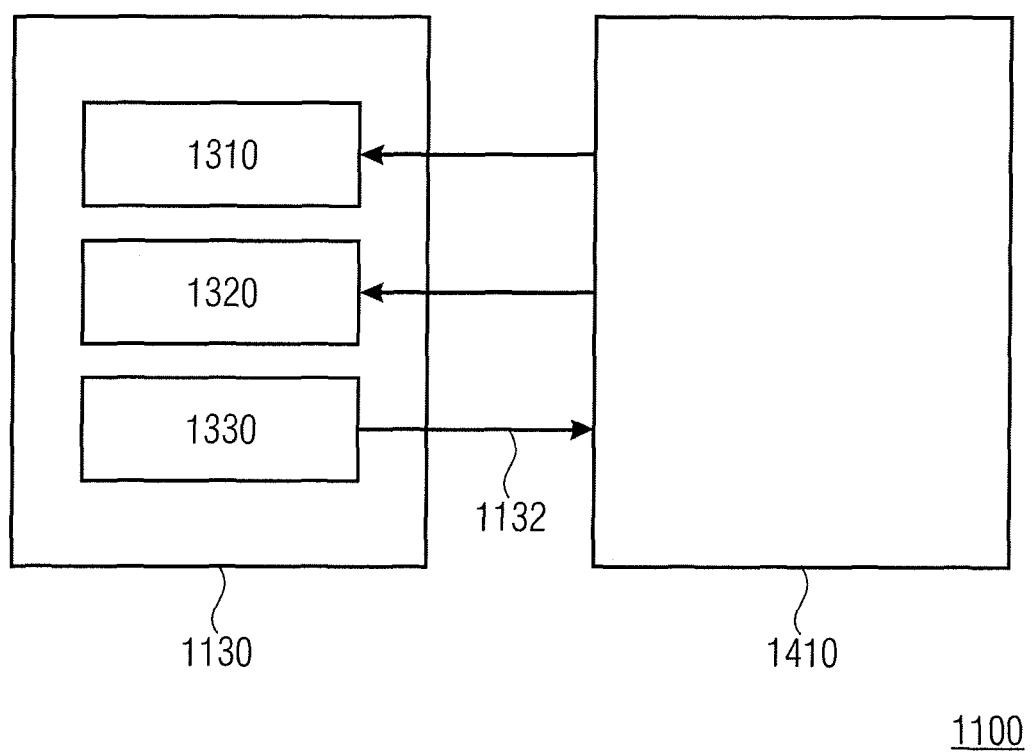
FIG. 1 shows a block diagram of an embodiment of a device for detecting a vital parameter with an optoelectronic sensor arrangement and a control means.

FIG. 1 shows a block diagram of an embodiment of a device 1100 for detecting a vital parameter comprising an optoelectronic sensor arrangement 1130 and a control means 1410.

The control means 1410 is coupled to the optoelectronic sensor arrangement, wherein the control means 1410 is implemented to activate or deactivate, or enable or disable the first light source 1310 or the second light source 1320 (see arrows from the control means 1410 to the first light source and second light source 1310, 1320), and is implemented to receive a signal from the light sensitive element 1330 comprising information on the intensity or light intensity of the received light. The signal is for example a voltage output by the light sensitive element and which depends in a known ratio on the light intensity of the incoming light.

The optoelectronic sensor arrangement 1130 is implemented to detect the vital parameter by means of light remission as it was already described above. The optoelectronic sensor arrangement 1130 comprises a first light source 1310 for generating light in a visible wavelength range, a second light source 1320 for generating light in a non-visible wavelength range or a wavelength range invisible for humans and a light sensitive element 1330 for receiving a portion of the light of the first and second light source 1310, 1320 reflected and remitted in a finger or in general for receiving a light in the wavelength range in which the first light source 1310 generates the visible light and the second light source generates the non-visible light.

The control means 1410 is implemented to switch on the second light source 1320 in temporal intervals to execute an evaluation of the light received from the light-sensitive element in the invisible wavelength range of the second light source with respect to whether a finger is applied to the optoelectronic sensor arrangement 1130, and to switch on the first light source 1310 as soon as the evaluation indicates that a finger is applied to the optoelectronic sensor arrangement 1130.

Here, the temporal intervals in which the second light source is switched on may be periodic, periodic with a fixed period or a decreasing period length, wherein the period duration or length decreases with time that passed since the last detection, or any other temporal intervals.

Further embodiments of the control means 1410 are implemented to switch off the first light source as soon as the above-mentioned evaluation indicates that no finger is applied to the optoelectronic sensor arrangement 1130.

Further embodiments of the control means 1410 are implemented to execute the above mentioned evaluation over a time period of the light, received from the light-sensitive element 1130, in the non-visible wavelength range of the second light source in order to detect a pulse parameter, e.g. a pulse wave, when a finger is applied to the optoelectronic sensor arrangement 1130, and accordingly switch on the first light source when the pulse parameter is detected.

From the temporal course of the light received from the light sensitive element or the signal 1132 generated depending thereon, the control means 1410 is for example implemented to detect the pulse wave itself, detect its special form (by means of corresponding evaluation algorithms), detect the frequency and/or pulse amplitude of the pulse or in general the presence of a signal, which allows a conclusion to the presence of a pulse and thus to a finger or similar things applied to the sensor arrangement 1130.

Only as an example for search evaluation algorithms, the following are mentioned: a) detecting a pulse or applying a finger when the signal 1132 comprises a certain number of zero crossings per time unit, b) detecting a minimum when falling below a minimum threshold value and a maximum when exceeding a maximum threshold value, wherein the temporal distance between the minimum and the maximum lies below a temporal threshold value, c) detecting a steepness of the increase, i.e. a maximum speed of increase of the signal amplitude of the previously lowpass filtered signal by means of detecting the maximum of the first deviation of the previously lowpass filtered temporal signal, d) detection of the significant signal structures with a known width, with the help of so-called opening operators and closing operators of a morphological analysis of the time signal, and e) analysis of the spectral density estimation, i.e. a weighting of the frequency portions.

In the following, the functioning of embodiments of an algorithm for detecting the pulse wave is explained based on a series of morphological, non-linear filter operations used mainly in image processing. The filter operators are the so-called "erosion" (see FIG. 3A), the "dilatation" (see FIG. 3B) and the resulting "opening" and "closing" also known as an "opening operation" or "morphological closing".

Figure 3A:
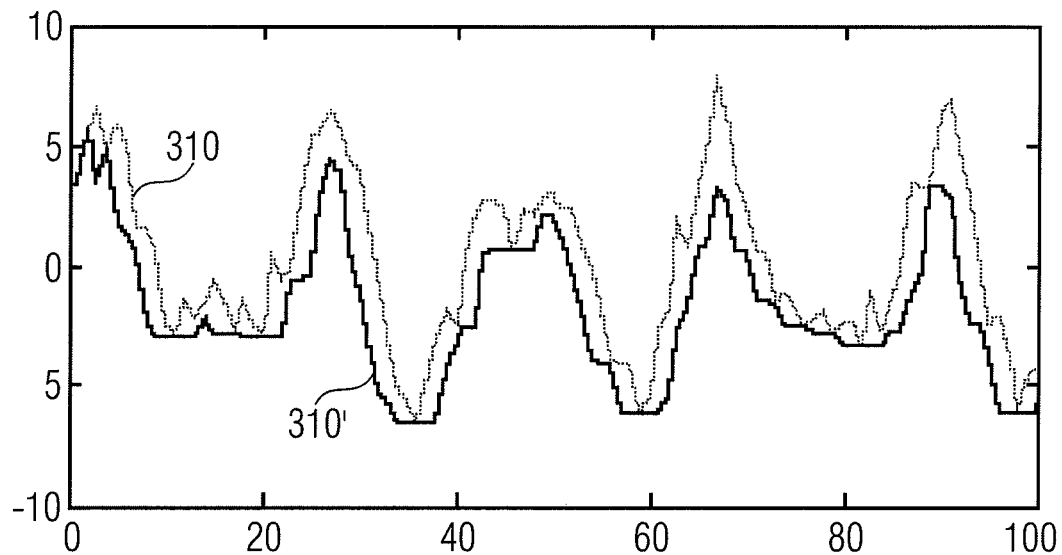
FIGS. 3A to 3D show exemplary courses of original signals and signals generated therefrom by means of morphological non-linear operators.

For each value of a digital signal f 310, the erosion operator determines the minimum of the surrounding M signal values and allocates the same as a new value. By this, positive signal ranges are removed and negative signal ranges are expanded. FIG. 3A shows the course of the original signal 310 and the signal 310' generated therefrom after erosion or after executing the erosion operation.

Figure 3B:
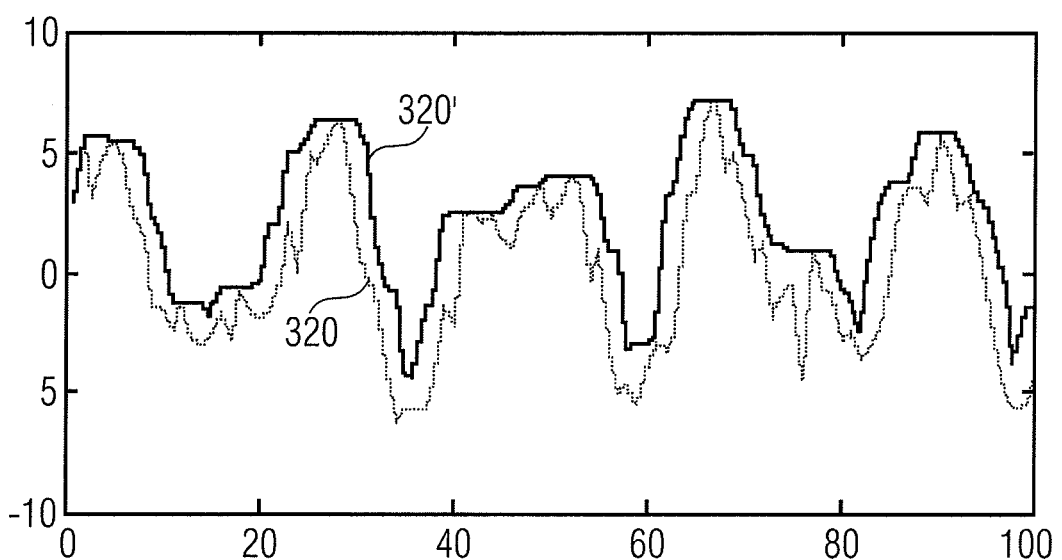

The dilatation operator determines, for each value of a digital signal f 320, the maximum of the surrounding M signal values and allocates the same as a new value. By this, positive signal ranges are expanded and negative signal ranges are removed. FIG. 3B shows an example of a course of an original signal 320 and a signal generated therefrom after the dilatation or after executing the dilatation operation.

Figure 3C:
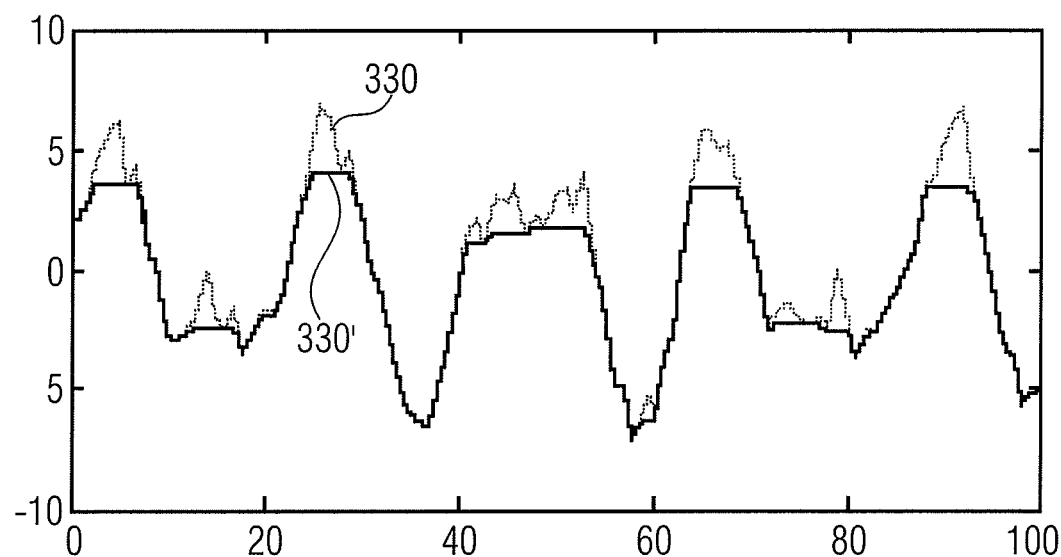

The opening operator is defined as erosion with a subsequent dilatation. Both operators together cause in this order the removal of all positive signal peaks within an interval from zero to M. FIG. 3C shows a course of an original signal 330 and the signal 330' generated therefrom after executing the opening operation.

Figure 3D:
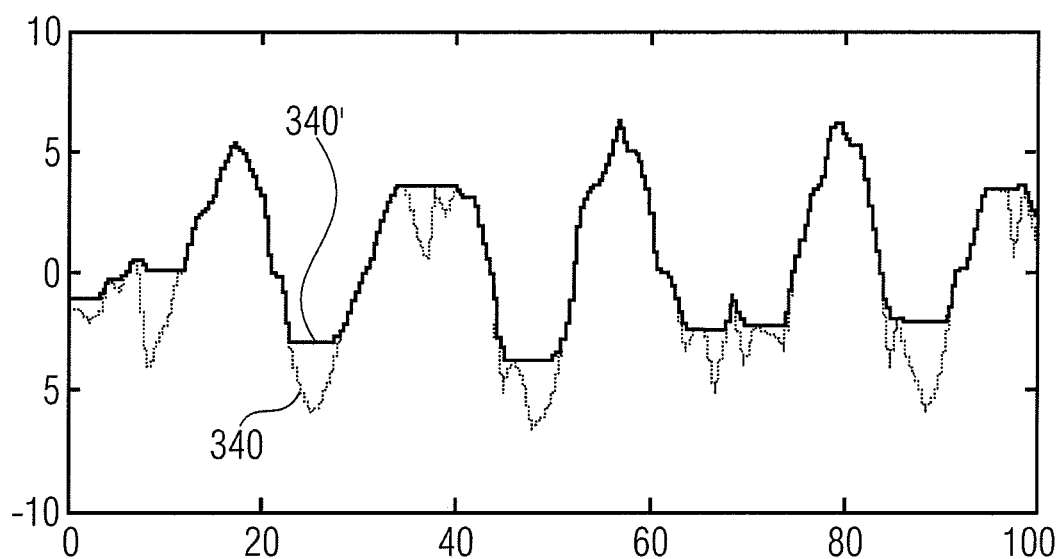

The closing operator is defined as a dilatation with a subsequent erosion. Both operators together in this order cause the removal of all negative signal peaks also referred to as pits, within an interval from zero to M. FIG. 3D shows the course of an original signal 340 and the signal 340' generated by applying a closing operation to the output signal 340, after "closing".

Due to their functioning, with the help of the opening and closing operators, on the one hand high-frequency noise in the form of peaks, pits or similar things may be removed from an input signal and on the other hand significant signal structures with a known width may be detected, like e.g. QRS complexes in an electrocardiogram or similar things.

The present invention further provides a method for detecting a vital parameter by means of an optoelectronic sensor arrangement 1130 as it was described before, for example with reference to FIG. 1. The method here comprises the steps explained in the following.

Switching on the second light source 1320 in temporal intervals.

Evaluating the light received from the light-sensitive element 1330 in the invisible wavelength range of the second light source 1320 with respect to whether a finger is applied to the optoelectronic sensor arrangement 1130 and switching on the first light source as soon as the evaluation indicates that a finger is applied to the optoelectronic sensor arrangement 1130.

For the method, the disclosures according to the device for detecting a vital parameter apply.

As a further embodiment of the method for detecting a vital parameter, in the following briefly a realization is described in which the light remission sensor or the optoelectronic sensor arrangement 1130 is integrated in a gear level knob of a vehicle. Here, the infrared diode 1320 is switched on simultaneously with the sensor 1130. The signal from the measurement photodiode 1330 is continuously requested or scanned and evaluated to be able to determine whether the finger of the driver is positioned opposite the optical sensor 1130 and the pulse waves may be detected. As soon as a pulse wave is detected, the red diode is additionally switched on and the standard routine for the pulse oxymetric measurement is requested. At this time, the finger is placed opposite the optical sensor 1130 and the red light of the red diode is shielded. As soon as the driver takes away his finger from the optical sensor 1130, this is regarded as a loss of optical contact between the finger and the sensor 1130 and the red diode 1310 is switched off again. The algorithm further continues the polling routine at the infrared channel.

Figure 2:
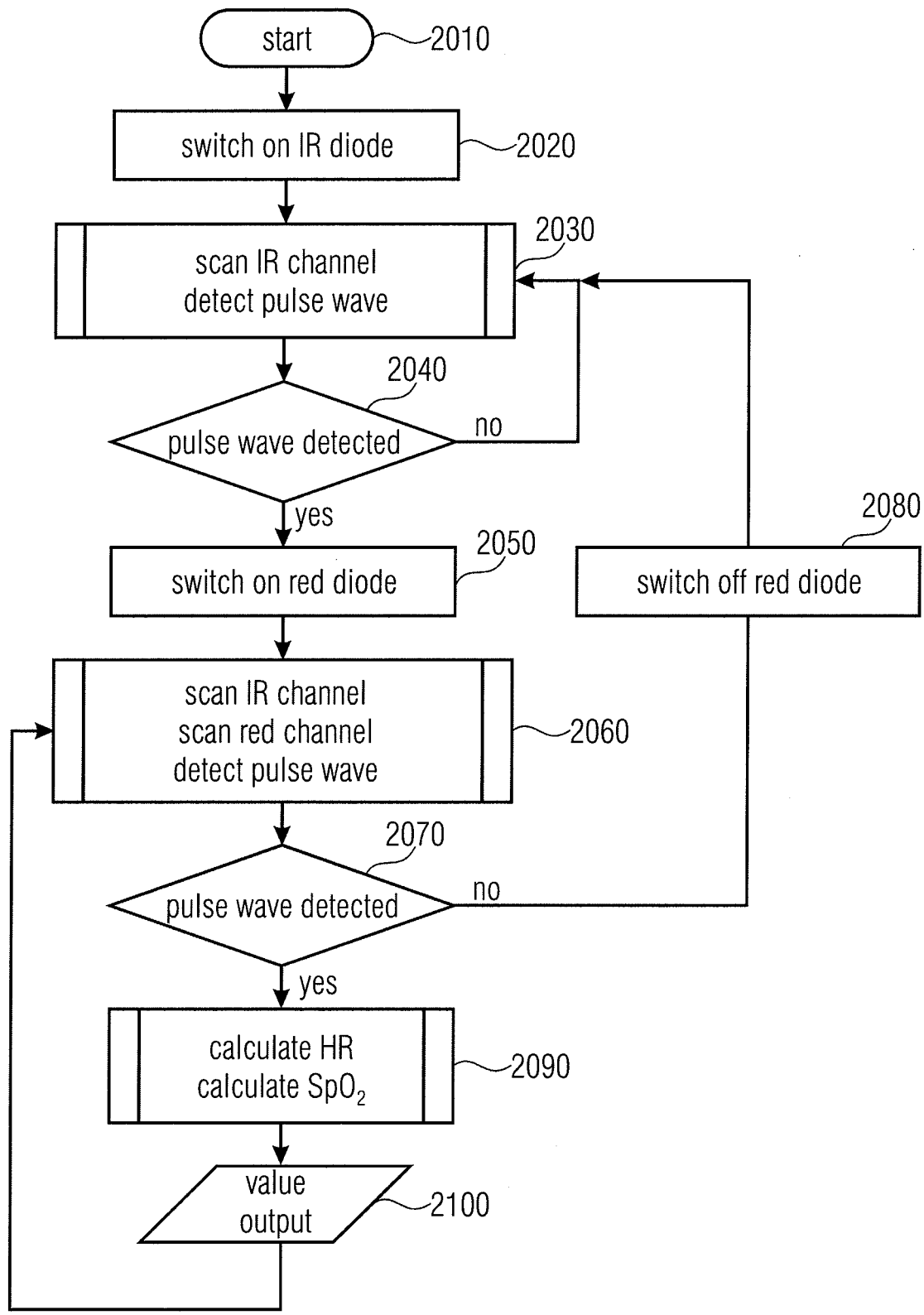
FIG. 2 shows a flow chart of an embodiment of a method for detecting a vital parameter.

In the following, an embodiment of this method for detecting a vital parameter is described in detail with reference to the flow chart illustrated in FIG. 2.

In step 2010 the device 1100 or the method for detecting a vital parameter is started and in step 2020 the infrared diode (IR diode) is switched on together with the optoelectronic sensor arrangement 1130. In step 2030 the infrared channel (IR channel) or the signal 1132 of the light sensitive element is scanned and, as described above, evaluated for example to detect a pulse wave as an indication whether a finger is applied. It is tested in step 2040 whether a pulse wave was detected. If no pulse wave was detected (no), step 2030 is repeated. If a pulse wave is detected (yes), in step 2050 the red diode 1310 is switched on and in step 2060 the infrared channel (IR channel) and the red channel are scanned. It is further tested in step 2060 whether further a pulse wave is detected (step 2070). If no pulse wave is detected (no), in step 2080 the red diode 1310 is switched off again and the method continues with step 2030. If further a pulse wave is detected (yes), the standard routine for the pulse oxymetric measurement in step 2090 is executed. Here, for example, based on the scanned infrared and red light or the signal 1132 of the light sensitive element resulting therefrom the pulse rate or heart rate HR and/or the oxygen saturation $SpO_2$ of the blood are calculated, i.e. in other words the standard routine for measuring the one or several vital parameters is executed. In step 2100 these values or vital parameters are then output, for example to a driver information system or to a doctor's PC. After step 2100 the method continues with step 2060 and the same is repeated until no pulse wave is detected.

With reference to the explanations above, embodiments also provide a "switch-on device of an optical sensor for detecting a pulse wave of the driver in the gear lever knob" and/or a "method for controlling an optical sensor for the detection of the pulse wave of the driver in the gear lever knob".

Here, the operation of the sensor is made optically invisible for the user or driver.

Depending on the circumstances, the embodiments of the inventive method may be implemented in hardware or in software. The implementation may be executed on a digital storage medium, in particular a floppy disk, CD or DVD having electronically readable control signals which may cooperate with a programmable computer system so that one of the embodiments of the inventive methods is executed. In general, the embodiments of the present invention also consist in software program products or computer program products or program products having a program code stored on a machine readable carrier for executing an embodiment of the inventive method, when one of the software program products is executed on a computer or on a processor. In other words, an embodiment of the present invention may thus be realized as a computer program or software program or program having a program code for executing an embodiment of an inventive method, when the program is executed on a processor. Here, the processor may be formed by a computer, a chip card, a digital signal processor or another integrated circuitry.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device for detecting a vital parameter, comprising:
    an optoelectronic sensor arrangement for detecting the vital parameter by means of light remission at a finger, wherein the optoelectronic sensor arrangement comprises a first light source for generating light in a visible wavelength range, a second light source for generating light in a non-visible wavelength range and a light sensitive element; and
    a controller which is implemented to switch on the second light source in temporal intervals, execute an evaluation of the light received from the light-sensitive element in the invisible wavelength range of the second light source with respect to whether a finger is applied to the optoelectronic sensor arrangement and to switch on the first light source as soon as the evaluation indicates that a finger is applied to the optoelectronic sensor arrangement;
    wherein the controller is implemented to execute an evaluation over a temporal course of the light received from the light sensitive element in the invisible wavelength range of the second light source to detect a pulse parameter when a finger is applied to the optoelectronic sensor arrangement and to switch on the first light source when a pulse wave is detected.

2. The device according to claim 1, wherein the controller is implemented to switch off the first light source as soon as the evaluation indicates that no finger is applied to the optoelectronic sensor arrangement.

3. The device according to claim 1, wherein the second light source and the light sensitive element are arranged so that the light received from the light-sensitive element is a portion of the light generated by the second light source remitted by the applied finger.

4. The device according to claim 1, wherein the pulse parameter is a pulse wave, a pulse frequency or a pulse amplitude.

5. The device according to claim 1, wherein the vital parameter is an oxygen saturation of the blood.

6. A method for detecting a vital parameter by means of an optoelectronic sensor arrangement for detecting the vital parameter by means of light remission, wherein the optoelectronic sensor arrangement comprises a first light source for generating light in the visible wavelength range, a second light source for generating light in a non-visible wavelength range and a light sensitive element, and wherein the method further comprises:
    switching on the second light source in temporal intervals;
    evaluating the light received from the light-sensitive element in the invisible wavelength range of the second light source with respect to whether a finger is applied to the optoelectronic sensor arrangement; and
    switching on the first light source as soon as the evaluation indicates that a finger is applied to the optoelectronic sensor arrangement;
    wherein an evaluation over a temporal course of the light received is executed from the light sensitive element in the invisible wavelength range of the second light source to detect a pulse parameter when a finger is applied to the optoelectronic sensor arrangement and to switch on the first light source when a pulse wave is detected.

7. The method according to claim 6, comprising:
    switching off the first light source as soon as the evaluation indicates that no finger is applied to the optoelectronic sensor arrangement.

* * * * *